Figure 1:
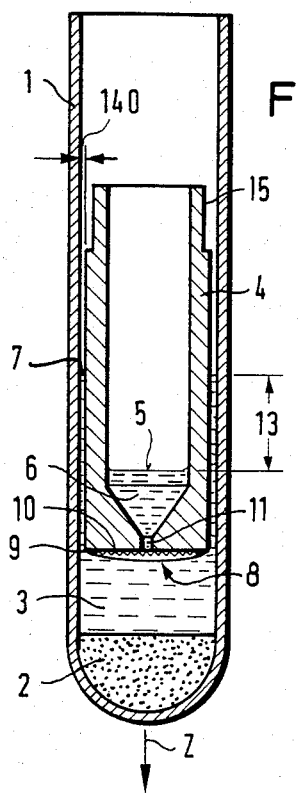

United States Patent [19]

Nussbaumer et al.

[11] Patent Number: 4,522,713
[45] Date of Patent: Jun. 11, 1985

[54] APPARATUS FOR STATIC MEMBRANE FILTRATION

[75] Inventors: Dietmar Nussbaumer; Horst Perl; Khuong T. Vinh, all of Göttingen, Fed. Rep. of Germany

[73] Assignee: Sartorius GmbH, Gottingen, Fed. Rep. of Germany

[21] Appl. No.: 555,636

[22] Filed: Nov. 25, 1983

[30] Foreign Application Priority Data

Nov. 26, 1982 [DE] Fed. Rep. of Germany ....... 3243864

[51] Int. Cl.³ .................... B01D 33/00; B01D 35/02
[52] U.S. Cl. .................... 210/136; 210/324; 210/335; 210/359; 210/406; 210/446; 210/472; 210/927
[58] Field of Search ........... 210/359, 515, 518, 500.2, 210/927, DIG. 24, 136, 324, 335, 406, 446, 472

[56] References Cited

U.S. PATENT DOCUMENTS

| | | | |
|---|---|---|---|
| 3,661,265 | 5/1972 | Greenspan | 210/359 |
| 3,799,342 | 3/1974 | Greenspan | 210/359 |
| 3,870,639 | 3/1975 | Moore et al. | 210/359 |
| 3,932,277 | 1/1976 | McDermott et al. | 210/359 |
| 3,954,614 | 5/1976 | Wright | 210/359 |
| 3,960,727 | 6/1976 | Hochstrasser | 210/359 |
| 4,057,499 | 11/1977 | Buono | 210/359 |
| 4,131,549 | 12/1978 | Ferrara | 210/359 |
| 4,253,963 | 3/1981 | Franken et al. | 210/500.2 |
| 4,302,270 | 11/1981 | Nicolet | 210/500.2 |

Primary Examiner—Richard V. Fisher
Assistant Examiner—W. Gary Jones
Attorney, Agent, or Firm—Balogh, Osann, Kramer, Dvorak, Genova & Traub

[57] ABSTRACT

In a filtration apparatus for fluids and liquids having an external vessel, in particular a centrifuge tube and a filter unit disposed in the liquid, the medium to be filtered is under excess pressure and in contact with the filter element of the filter unit and for the static membrane filtration on the outer side of the filtration unit facing the vessel bottom a filter membrane is arranged with the filtration-active layer towards the outside.

17 Claims, 17 Drawing Figures

APPARATUS FOR STATIC MEMBRANE FILTRATION

The invention relates to a filtration vessel having an outer tube, in particular centrifuge tube, and a filter unit disposed floating therein and open towards the air space, the medium to be filtered being under an excess pressure in contact with the filter and outer accelerations seen from the sample to be filtered having no vector in the direction of the filter.

Static filtration is the simplest filtration method. In it, the medium to be filtered stands under an elevated pressure in contact with the membrane without any forced flows. According to the prior art it can be used successfully when only very small substance amounts must be deposited from the suspension or solution as is the case for example in recovering sterile filtrates from weakly germinated solutions.

However, the higher the concentration of the dissolved or suspended substances to be separated in the static filtration the more the attainable filtration rates (filtrate amount per area and time) are impaired by the accumulation of the components to be separated at the membrane surface.

However, it is not only the higher technical expenditure which makes the use of correspondingly larger filter areas impracticable in many cases. In particular in analytical filtration operations, in which a complete as possible recovery of the concentrate or filtrate and the unfalsified composition thereof are important, filter areas must be used which are as small as possible.

It is obvious that large filter areas also result in correspondingly large losses of adhering filtrate or concentrate. In addition, however, the composition thereof can also be undesirably changed by the filter material. On the one hand, most filter materials, in particular ultrafiltration membranes, contain auxiliary agents which can be washed out (wetting agents, softeners, glycerin, bactericides, etc...) which can be troublesome in higher concentrations but the washing out of which previously would lead to dilution of the sample. On the other hand, by specific or unspecific adsorption effects filter materials can change the composition of the sample both in its total concentration and in the concentration ratio of the individual components to each other. Examples of this, which will be discussed hereinafter, are the adsorption of unbonded pharmaceutical compositions in the ultrafiltration of serum and the partial protein adsorption in the concentrating of proteins in urine.

Although the disadvantages of static filtration can be largely overcome by the principle of tangential overflow using pumps, this is not practical with small and minute volumes because of the losses which occur.

The problem underlying the invention is to avoid falsifications in the extraction of concentrate or filtrate in simpler manner than hitherto even with minute amounts and to permit the automation of the filtering operations.

This is achieved with an apparatus of the type mentioned at the beginning surprisingly in that for the static membrane filtration on the outside of the floating hollow body a membrane is disposed having the filtration-active layer towards the outside.

Preferably, as driving force of the filtration use is made of the hydrostatic pressure difference of at least 0.5 bar resulting from the level difference between the filtration medium and filtrate and the centrifugal acceleration, the apparatus being so designed that the centrifugal acceleration seen from the solution to be filtered has no vector in the direction of the membrane.

In the arrangement according to the invention the simplicity of the apparatus is astonishing and is of particular importance also with regard to the production of one-way or disposable apparatuses.

The static filtration in the acceleration field of a centrifuge or gravitation is employed in such a manner that the migration direction of the filtrate is different to the direction of the acceleration.

In contrast to known apparatuses for static filtration, in which centrifuge acceleration is also used to produce the effective hydrostatic pressure difference (for example German patent 19 06 179), in the apparatus according to the invention the centrifugal acceleration has no vector in the direction of the membrane. This avoids the settlement on the membrane of depositable constituents or the possibility of the concentrate formed (which generally has a higher density than the staring solution), accumulating on the membrane. The same applies when the filtration is carried out under the action of gravity in vacuum operation, the effect being of course correspondingly less pronounced.

Moreover, in the apparatus according to the invention it is achieved that during the filtration the movable membrane can follow the sinking sample level and until completion of the concentration operation is wetted over the complete area by the filtration medium, i.e. the effective filtration area remains unchanged during the entire operation.

Because of the simple construction of the apparatus the production costs are kept low.

Expediently, the filter insert includes following the stuck-on membrane a bore from which the filter insert widens inwardly up to the wall thickness of the thin hollow filter insert.

A particular advantage to be mentioned is the module system realized for some embodiments and it is astonishing how few parts are necessary for versatile use, permiting economic production.

Both in operation in vacuum and with centrifuge operation the apparatus is held together by external pressure without threads, etc...

Advantageously, for larger sample amounts floats are provided having a removable filter support and interchangeable membrane, the bottom of the float being made open with extension for insertion of the filter support.

The problem underlying the invention is frequently encountered in biochemical or medical analysis and in pharmaceutical research.

One example is the separation of proteins prior to column chromatographic determination of amino acids (Proteins render the column filling useless by irreversible bonding. Enzymatic protein hydrolysates and biological fluids must therefore be freed from proteins before the amino acid analysis.)

A further application is the determination of free (not protein-bonded) substances (e.g. pharmaceutical compositions) in the blood of patients.

Further use examples are the enrichment of enzymes, pyrogens or viruses for increasing detectability.

The embodiments of the invention in which by using a concentrate vessel a high and defined concentration factor is achieved may be used for concentrating proteins in urine or Lignor cerebrospina before their electrophoretic investigation, which is of importance in medical diagnostics.

In addition to the aforementioned advantages the apparatus according to the invention provides a small filter area and thus avoids adsorption losses. By effectively avoiding concentration polarization a high filtration rate is achieved. The macromolecules are not mechanically stressed. A minimum air contact of the sample arises and thus also practically no gas exchange with the atmosphere. The filtration can be carried out with a laboratory centrifuge without further aids. The simultaneous filtration of a large number of samples is possible.

Thus, in general the float dips partially into the sample in the centrifuge tube. As a result, the membrane is a hydrostatic pressure which under the influence of the centrifugal acceleration reaches several bars. In this case, the filtrate gathers in the interior of the float. Whereas normally angled-head and oscillating-head centrifuges can be equally well used, in the presence of emulsified lipids, for example milk, and angled-head centrifuge must be used to avoid covering of the membrane.

Figure 2:
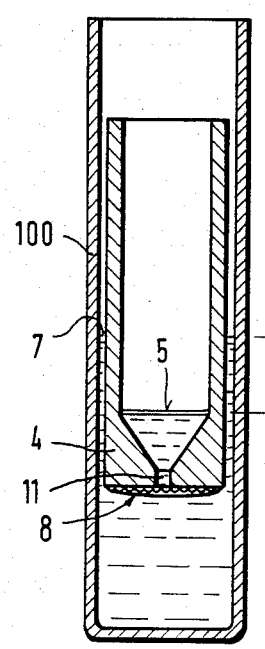
Figure 3:
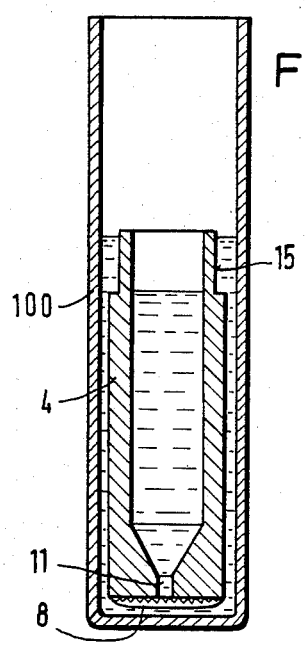
Figure 4:
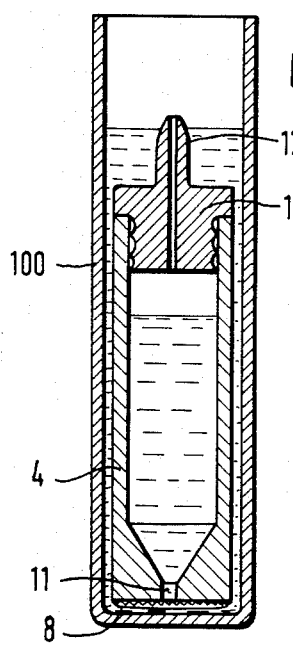
Figure 5:
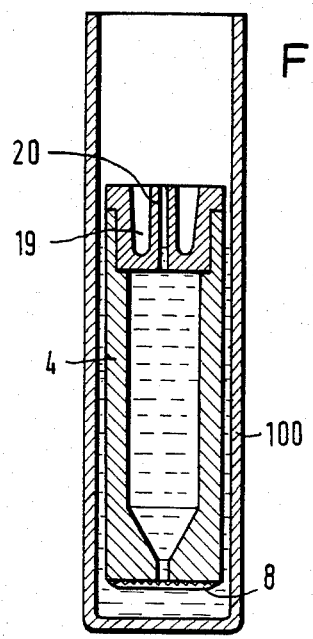
Figure 6:
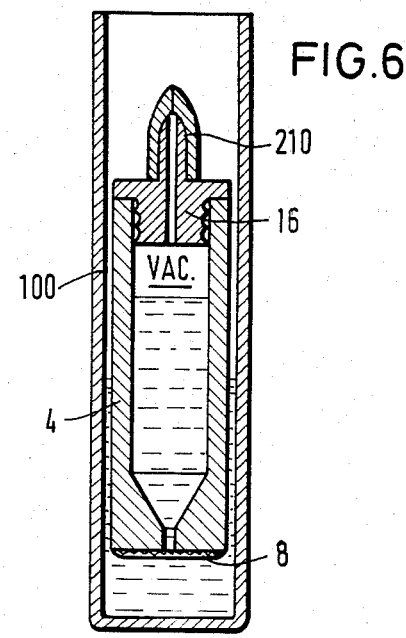
Figure 7:
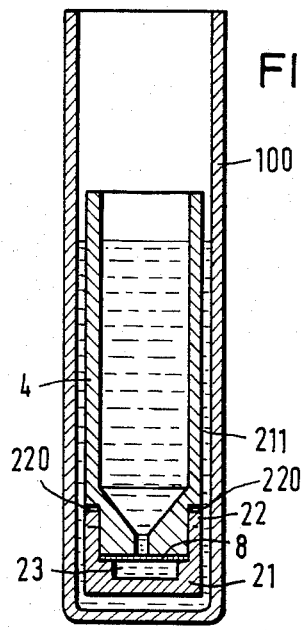
Figure 7A:
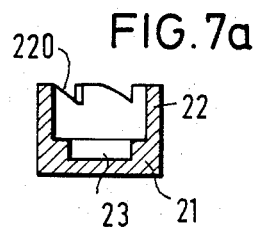
Figure 8:
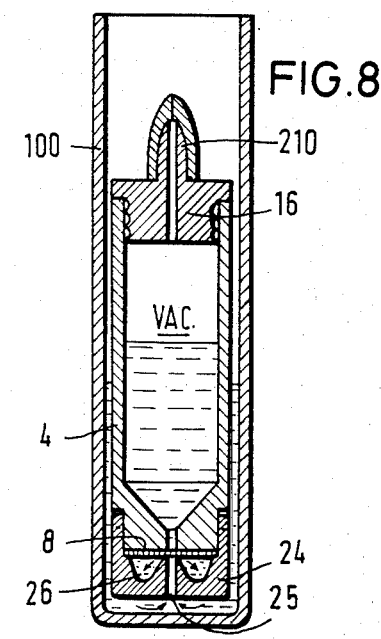
Figure 9:
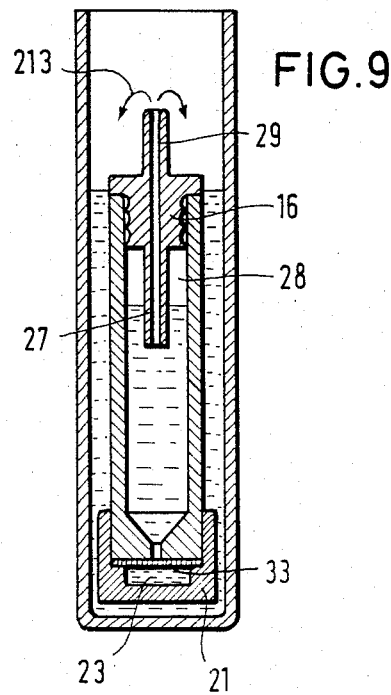
Figure 10:
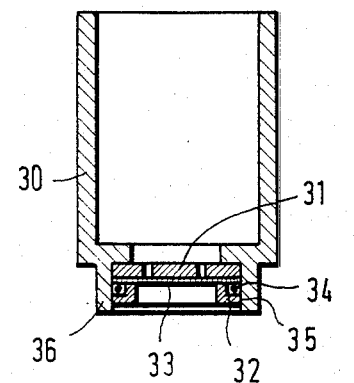
Figure 11:
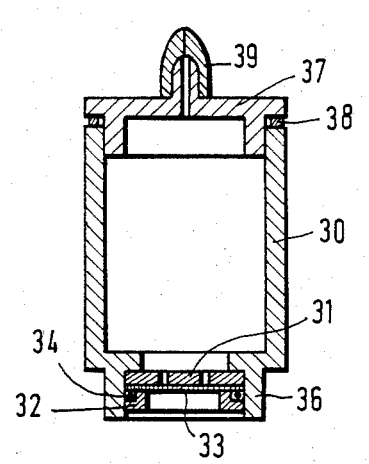
Figure 12:
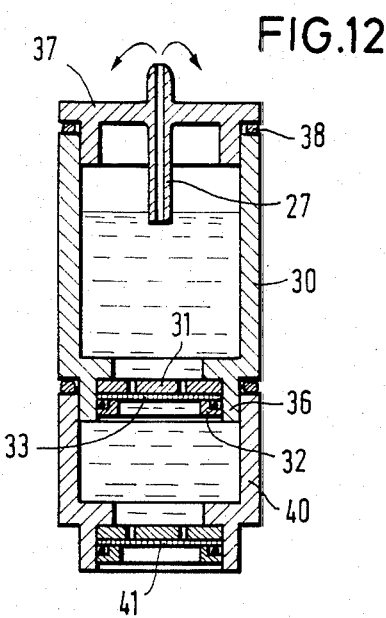
Figure 13:
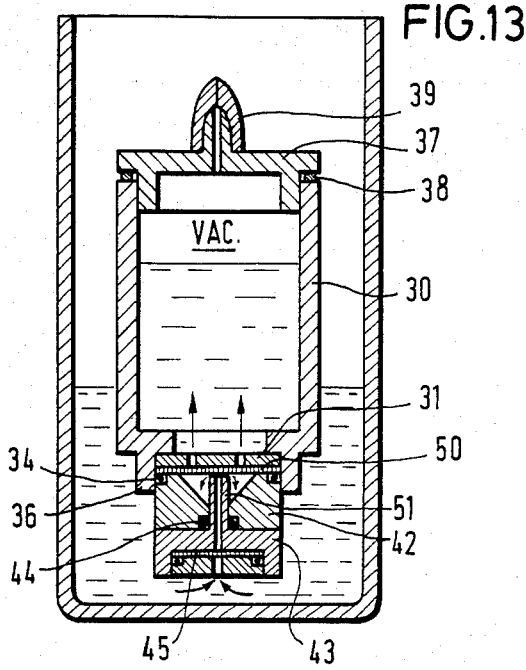
Figure 16:
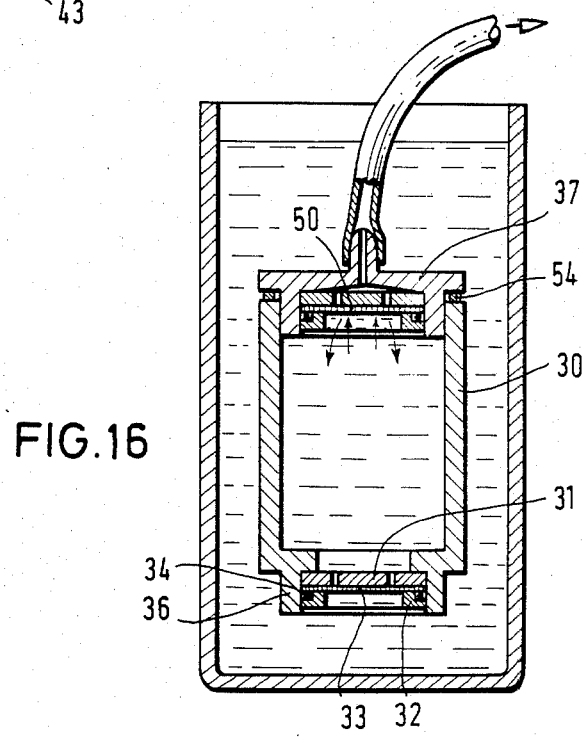
Figure 14:
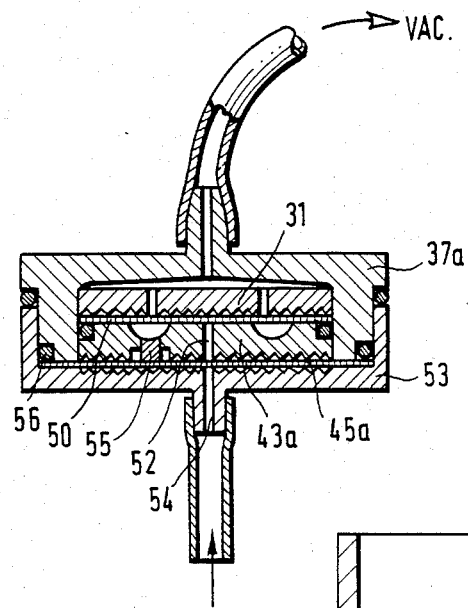
Figure 15:
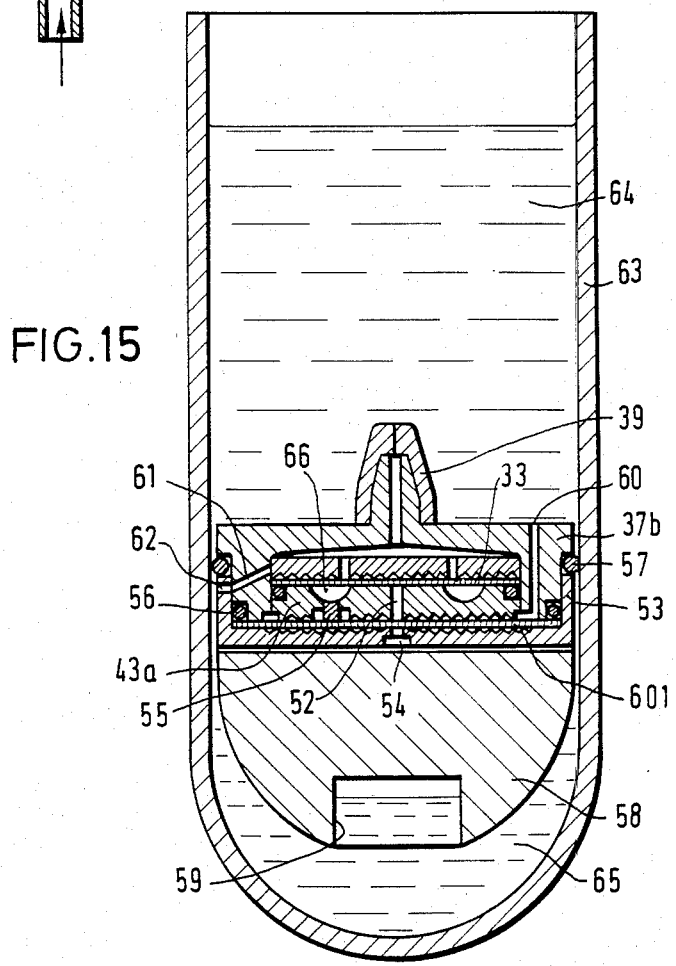

Examples of embodiments of the invention will now be explained in detail with the aid of the attached drawings, wherein:

FIG. 1 shows a first embodiment;
FIG. 2 shows a second embodiment;
FIG. 3 shows a modification;
FIG. 4 shows a modification with an additional element;
FIG. 5 shows a modification for a specific purpose;
FIG. 6 shows an embodiment for vacuum operation;
FIG. 7 shows a special embodiment particularly suitable for practice with minimum residual volume;
FIG. 7a shows a partial section of a concentrate vessel;
FIG. 8 shows a modification without any substance loss in the residual volume;
FIG. 9 shows an embodiment for intermittent centrifuging;
FIG. 10 shows an embodiment for larger sample amounts;
FIG. 11 shows a modification of FIG. 10;
FIG. 12 shows an embodiment which is particularly suitable for diafiltration;
FIG. 13 shows an embodiment for concentrating with vacuum operation;
FIG. 14 shows a particularly simple modification;
FIG. 15 shows an embodiment with buoyancy body;
FIG. 16 shows an embodiment for diafiltration and vacuum operation.

An embodiment for direct recovery of ultrafiltrate from blood is illustrated in FIG. 1 (condition after the start of the filtration). The constituents formed (blood corpuscles) 2 are already at the bottom of the centrifuge tube 1, and the filtration insert (hollow body/float) 4 with membrane 8 is floating on the plasma 3. The lateral distance or gap 140 between the insert 4 and tube 1 has been exaggerated for clarity and is about 0.1 mm. (With the usual conical tubes the inner dimension in the lower portion is decisive.) The reduced portion 15 serves as a store for rising liquid and prevents the capillary action after switching off the centrifuge. The membrane 8, preferably an asymmetrical ultrafiltration membrane with a separation limit of 20 000 Daltons, is connected with the active (filtration-effective) side outwards by means of a welding or adhesive edge 9 to the insert 4 in such a manner that no transverse flow can take place through the membrane in this region (as is known, ultrafiltration membranes have under the filtration-active layer a relatively coarse-pore protein-permeable support layer). If therefore the punched edge of the membrane is left open, which is the case when using adhesives which do not penetrate into the support layer, the active layer may be "infiltrated" by the protein solution. With the preferred method, thermal welding or fusion, a tight seal is guaranteed.

The filtrate 6 flows after passing through the membrane 8 through a system made in a manner known per se of fine passages 10 and the bore 11 and collects in the interior of the insert 4. The lower portion of the interior is preferably made conical to facilitate complete removal of the filtrate.

The driving force of the filtration is the hydrostatic pressure difference which results from the level difference 13 between the plasma level 7 and the filtrate level 5 under the influence of the centrifugal acceleration. Although the pressure difference becomes increasingly smaller as the filtration progresses, the filtration rate is not influenced thereby to this extent because with asymmetrical ultrafiltration membranes a rise of the filtration-active pressure difference beyond a certain amount which depends upon the separation limit of the membrane used does not effect any appreciable increase in the filtration performance (a level difference of 3 mm corresponds with a centrifugal acceleration of 3000 g to a pressure difference of 0.9 bar).

An accumulation of the concentrated protein at the membrane surface is avoided in that due to its high density (an increase in the protein concentration by 1 g/100 ml corresponds approximately to a density increase of 0.004 g/ml) the concentrate migrates in the direction of the centrifugal acceleration Z by convection back into the starting solution and mixes with the latter.

In the use described here it is desirable to obtain as much ultrafiltrate as possible from as little blood as possible. With blood, the limiting factor is the oncotic (colloid-osmotic) pressure occurring in the concentrated plasma because the filtration comes to a stop when the oncotic pressure of the concentrate and the effective hydrostatic pressure difference are equal. In practice, the upper limit of the proportion of ultrafilterable fluid is about 50% of the starting volume, this value of course being dependent on the hematocrit values, protein concentration of the samples, revolution number of the centrifuge and the geometry of the apparatus and centrifuge.

In the filtration of diluted protein solutions the filtration can come to a stop prematurely if, as illustrated in FIG. 1, a tube with a round bottom is used because the insert 4 abuts on the rounded portion. Since most commercial centrifuge tubes have a round bottom, in these cases a hemispherical displacement body with flat upper side must be placed on the bottom of the tube if a maximum of filtrate volume is to be achieved.

FIG. 2 shows an embodiment with a flat float 4 and flat-bottomed centrifuge tube 100. The float sinks increasingly deeper by taking up filtrate; even if too much starting solution is present, the solution does not flow over the edge of the float into the filtrate when the float is made from a material of a density which is less than that of the solution. If this is not the case the amount of sample present must be limited. With concentrated solutions, for example blood or serum, the filtration comes to a stop at a predetermined protein concentration so that a larger sample amount can be chosen.

In FIG. 3, as in FIG. 1, in the upper portion of the float where no compressive strength is necessary the wall thickness can be reduced by a turned-down portion 15. As a result, at the instant of contact with the bottom starting solution is still present which can still be filtered without anything rising above the edge.

According to FIG. 4 the same purpose is fulfilled by the plug 16 which has a vent bore in the center and terminates in the tubular extension 17. The float may after completion of the filtration be completely filled. In this embodiment the hydrostatic pressure difference rises once again abruptly after the sinking of the float to the bottom of the centrifuge tube until it finally becomes zero in the course of the further filtration.

In the modification of FIG. 5 the maximum filtrate volume is predetermined. The plug itself is hollow (upwardly open cavity 19); the central vent tube 20 is again present. It is also not necessary to make the density of the wall material lower than that of the solution to be filtered. Thus, the float is always able to float. As soon as the filtrate in the tube has reached the outer level of the sample, the filtration comes to a stop.

According to FIG. 6 a reduced pressure in the float is used as driving force for the filtration. For example, a great number of apparatuses will be evacuated simultaneously in a vacuum drying chamber and check valves 210 fitted to the otherwise unchanged plugs 16. After ventilation of the chamber filtration begins. As example of a check valve, a valve similar to a bunsen valve (flexible tube closed on one side with incision in the longitudinal direction . In this case, a cap of silicone rubber with incision in the longitudinal direction is preferred) can be used. In contrast to the operation in the centrifuge, no residual volume of starting solution need be accepted.

A particularly important embodiment is shown in FIG. 7. Beneath the membrane a special concentrate vessel 21 can be fitted to the float. The objective of this embodiment is to minimize losses of dissolved substance which depend primarily on the magnitude of the surface wetted by the concentrate. This is achieved in that the concentration does not take place in the sample container but in a concentrate container in communication with the latter and having a volume corresponding to the desired concentrate amount. This simultaneously gives the advantage that it is impossible to erroneously concentrate to an excessive degree. To obtain low filtration times in spite of this step the sample must reach the membrane without mixing with the concentrate already formed. The concentrate vessel is made from a material of lower density than that of the medium to be filtered, in general an aqueous solution, and is thus pressed by its own buoyancy against the float so that it requires no fixed connection. The concentrate gathers in the cavity 23 whose volume defines the concentrate volume to be obtained. The side wall 22 of the vessel is continued up beyond the level of the membrane 8 which prevents the concentrate formed from escaping, the concentrate having in the case of protein solutions a higher density. For the supply of the starting solution no special measures need be adopted provided the concentrate vessel is not connected to the float in an absolutely sealed manner. The filter support 10 in this embodiment is preferably made slightly convex which prevents an air bubble from forming beneath the membrane 8. It is then not necessary for the concentrate vessel to be filled with liquid prior to the filtration because the air at the edge can completely escape. Because the starting solution has a lower density than the concentrate already formed, it spreads directly beneath the membrane 8 and is concentrated there without having mixed with the concentrate already formed. To facilitate removal of the concentrate vessel 21 after completion of the filtration and avoid spilling of the concentrate upon abrupt withdrawal of the float, the edge 22 can be provided at 220 with serrated withdrawal inclinations which are in engagement with corresponding recesses in the wall of the float. The withdrawal of the concentrate vessel in this case is by a rotational movement. The withdrawal inclinations may also be made in a manner permitting an engagement in different positions which enables different concentrate volumes to be preselected. The arrows indicate the flow path, a concentration arising in a predetermined ratio on the basis of the supply from the sample 211. In all embodiments the same reference numerals refer to identically acting parts. An embodiment similar to FIG. 6 for vacuum operation using the check valve 210 is shown in FIG. 8, in particular the concentrate vessel 24.

In this case the starting solution is not supplied from above but from below via the bore 25. The sample present can thus be completely filtered. The concentrate space in this case is an annular depression 26 whilst the bore 25 for the supply of the starting solution is led right up to the diaphragm 8.

No substance loss occurs in the residual volume.

When operated with an intermittently running centrifuge, as already mentioned above, the embodiment of FIG. 9 can be advantageous. Whereas in FIG. 7 a small amount of the starting solution remains unfiltered in the gap between float and outer tube, it may be desirable to recover completely the high-molecular substances in the solution. This is achieved in that a rinsing is carried out with a suitable liquid. If already formed filtrate is used for this purpose a falsification of the sample by the presence of low-molecular components or the lack of existing components is not possible. For example, the plug of FIG. 4 is used and has additionally at the lower side in the filter space the rise tube 27. If the interior of the float becomes filled with filtrate the air present can escape unrestricted until the filtrate level has reached the lower end of the rise tube 27. If the filtration continues the remaining air will be compressed at 28 to form an air cushion. If the hydrostatic pressure is removed by switching off the centrifuge the compressed air cushion 28 expands and displaces the portion of the filtrate which is disposed above the lower end of the rise tube 27. The filtrate now rises through the rise tube and the bore 29 in the plug back into the starting solution. When the centrifuge is switched on again a further portion of the dissolved substance passes into the concentrate vessel. With frequent intermittent running the substance amount dissolved in the solution can be transferred to the concentrate vessel to any desired degree of completeness. The conditions when stationary are indicated by the arrow 213.

Whereas hitherto particularly small sample amounts were involved, the embodiment of FIG. 10 is suitable for larger sample amounts. The float 30 has a downwardly open bottom and an annular extension 36 into which the filter support 31 is inserted. The membrane 33 and then the 0-ring 34 are placed thereon. The sealing force is provided by a clamp ring 32 which presses the 0-ring against the membrane 33 and the inner wall of the extension 36. The clamp ring 32 is held in position in turn by the friction between its outer surface 35 and the inner surface of the extension 36. Of course, a clamp ring which can be screwed in is also possible. The clamp ring 32 and filter support 31 are made from a material having a density lower than that of the starting solution so that during the centrifugation due to their buoyancy they are pressed against the float 30.

The basic apparatus of FIG. 10 may be modified in many ways: an embodiment for vacuum operation is shown in FIG. 11 which additionally to the parts shown in FIG. 10 comprises a cover 37 which is sealed with the 0-ring 38 against the float 30 and includes a pressure control valve 39 of the type described above. Embodiments result with interchangeable filter in the module system for several purposes using an intermittently running centrifuge (also explained in FIG. 9).

FIG. 12 again shows the rise tube and sample vessel in particular for diafiltration with intermittent centrifuging. On the other hand, the desalting, demineralizing or adsorptive separation of low-molecular fractions is possible. An analogously constructed further vessel (float) 40 is disposed externally on the float 30 and is made from a material of lower density than that of the medium to be filtered. This further vessel has below again a filter support with membrane 41. The small float 40 now contains the sample and is filtered through the membrane 33 into the large float.

The detachable filter support is of decisive importance in this case because the apparatus can be turned; the float 40 is then open at the top: the sample can be filled from above and the filter support and membrane fitted without an air bubble forming in the interior. In the example of the embodiment of FIG. 12 the float 40 carries a membrane 41 having a cut-off of 20 000 Daltons, the membrane 33 on the float 30 having a cut-off of 100 000 Daltons. If therefore the sample contains proteins having a molar weight of less than 100 000 Daltons, they can pass through the membrane 33 and into the filtrate. By the mechanism of the intermittently running centrifuge the filtrate is pressed outwardly in the stationary condition and thus reaches the membrane 41 and on passing through the latter is freed from proteins having a molar weight of more than 20 000; pure water or solvent migrate back to the sample. If this operation is carried out often enough by diafiltration the respective protein is washed out of the sample and remains in the external space.

It is obvious that between the vessel 30 and the float 40 further vessels 30 could be arranged in similar manner if the sample is to be separated into several fractions. The arrangement of the membranes is then expediently such that the sample is first filtered by the membrane with the highest cut-off and in the following vessels the membranes with the respective next lower cut-offs are used. The vessels provided for receiving the individual fractions are filled air-free with a suitable liquid before the start of the centrifugation.

In for example the desalting of a protein sample the filtrate chamber of the float 30 can partially be filled with a mixed-bed ion exchanger. The filtrate rises through the ion exchanger before on stopping of the centrifuge it reaches the outside again through the rise tube, i.e. the filtrate which passes into the outer space is desalted and on repeated centrifugation penetrates through the membrane 41 again into the sample. Active carbon can be introduced into the float 30 instead of the ion exchanger. The embodiment of FIG. 13 is for concentrating with vacuum operation. Measures are taken so that when the sample is completely used up the rising of air into the concentrate vessel 42 is prevented. In contrast to FIG. 11, a clamp ring is not inserted in the extension 36 of the float but a concentrate container 42 which first performs the same clamping function as the clamp ring but in addition defines a volume, i.e. the concentrate volume. Removably inserted in the concentrate container 42 is an insert 43 which is sealed by the sealing 44 with respect to the concentrate container 42 and reaches via a tubular extension 51 up to directly below the membrane. To remove the concentrate the apparatus is turned and the insert 43 withdrawn. For vacuum operation an additional filter 45 is provided which is clamped in the manner described above but represents a pore filter and has for example a pore size of 0.2 $\mu$. Filters of this type have the property in the wet condition of allowing air to pass only at a higher pressure. Thus, when there is no longer any sample present the filtration is terminated. This arrangement can also be used in the centrifuge, the filter 45 then being superfluous although it can also be used for prefiltration or sterile filtration. The pressure control valve 39 is omitted.

A particular simple embodiment is shown in FIG. 14 where components having the same function but of different design again have the same reference numerals but with an "a" affixed. In this case however, the connection of the cover 37a is directly to a vacuum flexible tube. Located in the cover is an ultrafilter 50 and beneath the concentrate vessel 43a a pore filter 45a. The concentrate vessel 43a is formed on its lower side as filter support with passages in the direction towards the central bore 52. The supply of the sample may be effected by placing the apparatus in a sample container or through a flexible tube from any desired vessel inserted into the bore 54.

The application pressure for the 0-ring 56 is by the housing 53. The concentrate is withdrawn after removal of the housing 53 and withdrawal of the rubber plug 55.

This arrangement may be used in conjunction with the float 30 and check valve 39 similar to FIG. 13 in vacuum operation without a closed vacuum tube or in conjunction with float 30 in the centrifuge.

A further preferred possible use with a slight modification of the components of FIG. 14 and additional use of the buoyancy body 58 is illustrated in FIG. 15. The modifications mentioned concern the additionally provided bores 61 and 60 in the cover 37b and the bore 62 in the housing 53. Instead of the pore membrane 45a of FIG. 14 there is the ultrafiltration membrane 601, with the filtration-active side towards the inside. Furthermore, the 0-ring seal 57 seals the gap between the cover 37b and centrifuge glass 63. The buoyancy body 58 mentioned preferably comprises no fixed connection to the housing 53 but may alternatively be made as a part thereof. The buoyancy body 58 may be an air-filled hollow body (air cushion) sealed all around which can withstand an external pressure of at least 3 bar, or may be entirely of foamed outwardly sealed material resistant to external pressure. The mean density, i.e. the mass divided by the external volume, is less than that of the medium to be filtered, preferably below 0.7 g/cm$^3$, mean densities below 0.5 g/cm$^3$ being particularly preferred. The mean density of the buoyancy body is matched to its dimensions so that with respect to the cross-sectional area of the centrifuge glass it exerts a lift of at least 1 g/cm² corresponding to a pressure difference of 1 cm water column.

The relationship between the quantities referred to is illustrated mathematically below:

V = outer volume of the buoyancy body 58 (cm³)
F = inner cross-sectional area of the centrifuge glass 63 (cm²)
$\rho_A$ = mean density of the buoyancy body 58 (g/cm³)
$\rho_{fl}$ = density of the medium to be filtered (g/cm³)
A = lift (g)
A/F = V/F($\rho_{fl} - \rho_A$) (g/cm²)
Requirement:
A/F $\geq$ 1 g/cm²)
Assumption:
$\rho_{fl} \approx$ 1 g/cm³)
1 $\leq$ V/F (1 $- \rho_A$)

The volume selected must therefore satisfy the relationship $$V \geq \frac{F}{1 - \rho_A}.$$

The smaller the mean density of the buoyancy body is made the smaller its volume can be and the greater the volume of the sample to be filtered.

The apparatus is used in the following manner: The buoyancy body 58 and the parts mounted in the arrangement illustrated are pushed down to the bottom of the centrifuge glass 63. The air present escapes via the pressure control valve 39. To keep the dead volume small the lower portion of the buoyancy body if preferably adapted to the interior of the centrifuge glass. The starting solution 64 is now introduced. It is thus disposed at the start of the filtration above the apparatus.

FIG. 15 illustrates the condition after the start of the centrifuging. Because of buoyancy the device has moved upwardly and filtrate 65 has already been formed below. The filtration is terminated when the device has risen completely to the top. The mode of operation of the apparatus is as follows: Under the action of the buoyancy body 58 a hydrostatic pressure difference forms between the filtrate 65 (beneath the seal 57) and the starting solution 64 and is defined by the equation:

$$\Delta P = \frac{V}{F} (\rho_{fl} - \rho_A) \cdot \frac{RZB}{1000} \cdot (bar)$$

RZB = relative centrifugal acceleration.

Of course, the density difference of the other components compared with the starting solution must be taken into account but it is not large when using plastics.

The starting solution 64 passes through the passage bore 60 (preferably at least 3 such bores are disposed at equal intervals) into the apparatus and flows along the membrane 601 to the passage bore 52 in the concentrate vessel. A partial filtration already occurs because the inner side of the cover 53 is constructed as filter support. The filtrate escapes through the bore 54 to the filtrate side. The already partially concentrated starting solution now flows from the center point of the membrane 33 outwardly and is further concentrated. The concentrate 66 collects in the annular concentrate space of the concentrate container.

The filtrate formed at the membrane 33 flows through the bore 61 in the cover 37b and the bore 62 in the housing 53 into the filtrate space (these bores may also be present several times).

The recess 59 at the lower side of the buoyancy body 58 encloses an air bell which is compressed by the hydrostatic pressure of the filtrate. In the manner already explained this air cushion expands, a corresponding volume thereby being conveyed through the bores 62 and 61 and the pressure control valve 39 back to the upper side of the apparatus (due to the friction between the seal 57 and centrifuge glass 63 the entire device is not pressed upwardly, the pressure control valve 39 opening beforehand). On renewed centrifuging residues remaining in the bore 60 and below the concentrate vessel 43a can be rinsed out. The recess 59 can also be dispensed with. In this case, by manually depressing the device back filtrate can be conveyed upwards for the rinsing.

At the membrane 601 the accelerating direction and filtration direction are the same as in conventional filtration apparatuses. Concentrate can therefore accumulate at the membrane. In the preferred uses, however, this is of minor importance because very diluted solutions are filtered and high concentrations are not reached until the membrane 33. The membrane 601 is only intended to reduce the necessary filtration time and can, when that is not necessary, also be omitted, provided the bore 54 is not present either.

After removal of the pressure control valve 39 the device can be withdrawn from the centrifuge glass 63 and the concentrate removed as described with regard to FIG. 14.

The devices described above operating with concentrate vessels must be operated in an oscillating-head centrifuge because in an angled-head centrifuge the concentrate would run over the edge.

If only the filtrate recovery or an only slight concentration of the sample is involved as in embodiments 1 and 10, fundamentally angled-head centrifuges can also be used but with a lesser filling level.

Moreover, FIG. 16 shows an embodiment for diafiltration with vacuum operation, the parts merely being fitted together. A vacuum is again applied and the rinsing liquid penetrates from below via the membrane 33. Provided below the cover 37 is a clamp ring 54; the lower part of the cover 37 is constructed like the extension 36 in the earlier figures. The sample is disposed within the float 30 and the rinsing liquid in the outer vessel.

We claim:

1. In a filtration apparatus for static membrane filtration of liquids, including an outer vessel comprising a centrifuge tube containing a liquid medium to be filtered, and having an open top and a closed bottom, and a filter unit provided with a filter element disposed in the liquid medium within said tube, the medium to be filtered being under excess pressure and in contact with said filter element of the filter unit, the improvement which comprises the filter unit having means defining an open upper end and a portion thereof at said upper end is reduced in wall thickness for storing rising liquid medium, means defining an unsealed gap or clearance situated between the filter unit and said centrifuge tube, and a filter membrane being disposed on the outside of the filter unit facing the bottom of said tube, the membrane having an edge and being sealed around said edge, and having a filtration active layer pointing outwardly thereof for filtering the medium so as to allow a filtrate thereof to collect in the filter unit.

2. The improvement according to claim 1, further comprising means for providing a level difference between the medium to be filtered and the filtrate which, under influence of centrifugal acceleration of said tube, results in a hydrostatic pressure difference of at least 0.5 bar, which serves as a driving force of the static membrane filtration, the centrifugal acceleration seen from the medium to be filtered having no vector in the direction of the membrane.

3. The improvement according to claim 1 or 2, wherein the membrane comprises an asymmetric ultrafiltration membrane and is connected to the filter unit such that the filtration active layer side thereof is externally sealed.

4. The improvement according to claim 1, wherein the filter unit comprises an upper portion and a lower portion and a hollow interior, having means defining a central bore, adjoining the membrane from which a lower portion of the interior widens conically inwardly up to the upper portion thereof.

5. The improvement according to claim 4, further comprising a plug defining a central vent bore and terminating in an extension for closing the hollow interior of the filter unit.

6. The improvement according to claim 5, wherein said plug is hollow and a vent tube is accommodated therein open towards the top thereof.

7. The improvement according to claim 8, further comprising a check valve being connected to said plug for closing the filter unit at the upper end thereof for reduced pressure operation.

8. The improvement according to claim 6, wherein said plug is provided on the lower side thereof with a rise tube.

9. The improvement according to claim 1, wherein the bottom of each of said centrifuge tube and the filter element is made planar.

10. The improvement according to claim 1, further comprising a concentrate vessel being fitted on the filter unit beneath the membrane, said concentrate vessel being made of a material of lower density than that of the medium to be filtered.

11. The improvement according to claim 10, further comprising a filter support which is made slightly convex.

12. The improvement according to claim 10, wherein said concentrate vessel is drawn upwardly and provided with serrations, and the filter unit is provided in the wall thereof with recesses corresponding to said serrations and engaged by said serrations.

13. The improvement according to claim 1, further comprising a larger filter unit for larger amounts of the medium to be filtered, having an open bottom provided with an extension, a removable filter support inserted into said extension and an interchangeable membrane placed thereon.

14. The improvement according to claim 13, for use in vacuum operation, further comprising a cover provided with a pressure control valve sealed against the filter unit, said cover and said extensions of the filter unit being identical in their dimensions, and one or more further filter units having their own filter support and their own membranes of different cut offs, being fitted externally to the filter unit, said one or more further filter units being made from a material of lower density than that of the medium to be filtered.

15. The improvement according to claim 14, wherein a concentrate vessel is sealed with respect to said cover and is constructed as a filter support, and a pore filter is disposed beneath said concentrate vessel, and a filter membrane is disposed in said cover.

16. The improvement according to claim 14, further comprising a concentrate vessel fitted on the filter unit beneath the membrane, a buoyancy body which acts on the filter unit with said concentrate vessel, and is adapted to the shape of the centrifuge tube, the buoyancy body having means defining a recess for accommodating an air cushion, said cover provided with means defining passage bores and having its inner side constructed as a filter support, and an ultra-filtration membrane carried by the inner side of the cover, and having its filtration active side pointing inwards, said concentrate vessel having means defining a bore for passing therethrough a starting solution flowing via the passage bores of said cover along the ultra-filtration membrane.

17. The improvement according to claim 1, further comprising a filter support of the filter unit designed for an external pressure of at least 3 bar and an immersion depth in a freely floating condition in a liquid medium of a density of 1 g/cm$^3$, being at least 10 mm.

* * * * *